United States Patent [19]
Cox et al.

[11] Patent Number: 6,030,334
[45] Date of Patent: Feb. 29, 2000

[54] METHOD AND APPARATUS FOR TREATING AND PREVENTING ARTERIOSCLEROSIS

[75] Inventors: Kenneth W. Cox; Brad Borgard, both of Cedar Park, Tex.

[73] Assignee: Sulzer Carbomedics Inc., Austin, Tex.

[21] Appl. No.: 09/144,885

[22] Filed: Sep. 1, 1998

[51] Int. Cl.$^7$ .................................................. A61M 37/00
[52] U.S. Cl. ................................................................ 600/12
[58] Field of Search ............................................ 600/9–15

*Primary Examiner*—John P. Lacyk
*Attorney, Agent, or Firm*—Timothy L. Scott; Philip S. Lyren; Kenneth S. Barrow

[57] ABSTRACT

A method and apparatus for treating and preventing arteriosclerosis includes a magnet located inside the human body adjacent an artery. The magnet generates magnetic flux through the artery. At least a portion of the magnetic flux has a component perpendicular to the direction of blood flow through the artery.

40 Claims, 11 Drawing Sheets

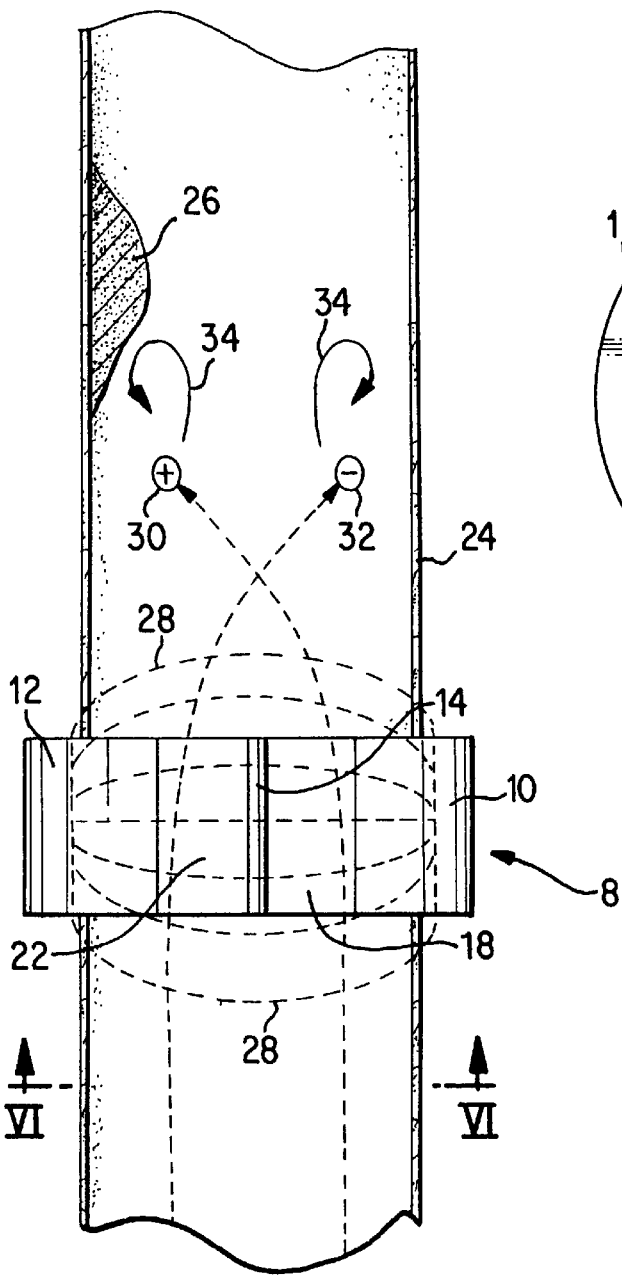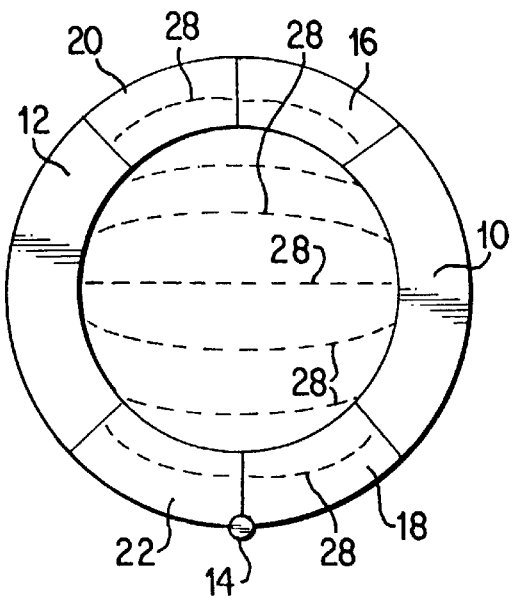
FIG. 5
FIG. 6

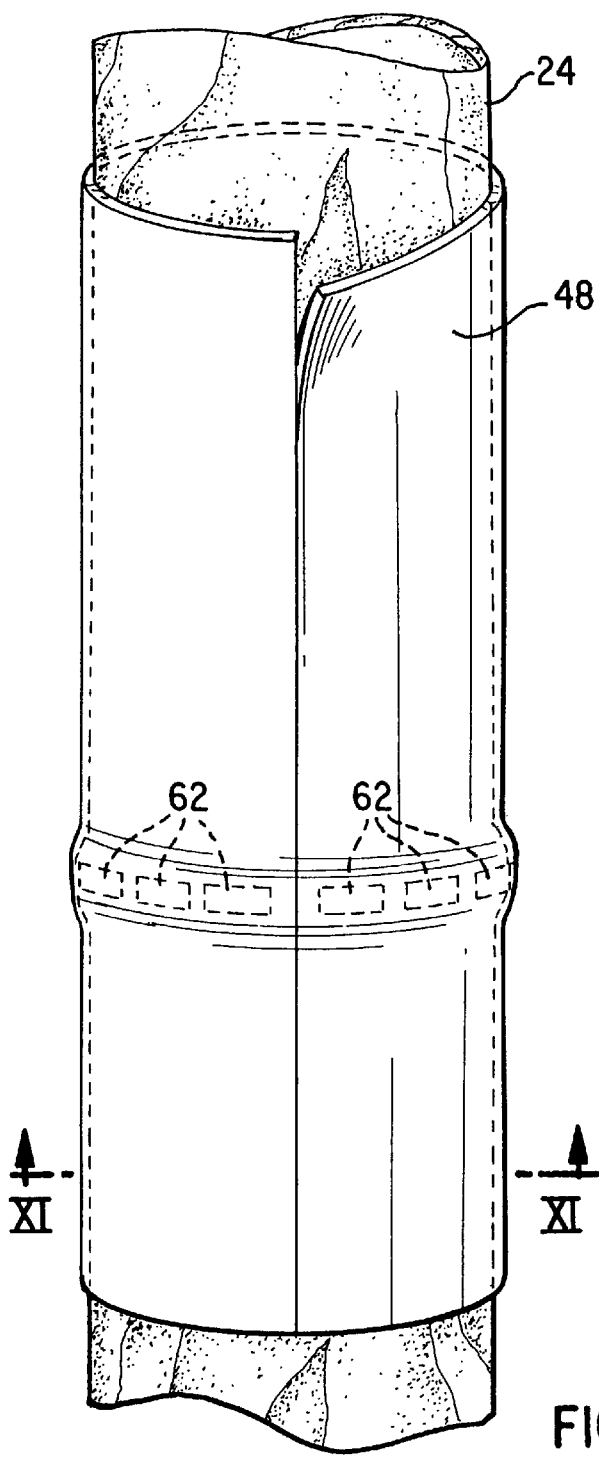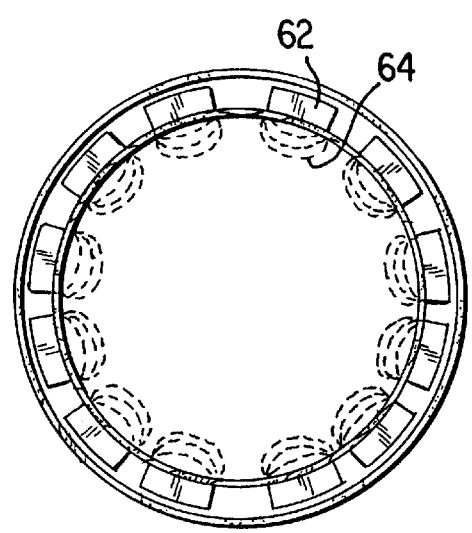
FIG. 11
FIG. 10

METHOD AND APPARATUS FOR TREATING AND PREVENTING ARTERIOSCLEROSIS

FIELD OF THE INVENTION

The field of the invention is treating and preventing arteriosclerosis. More particularly, the invention deals with treating and preventing arteriosclerosis using magnets.

BACKGROUND OF THE INVENTION

Arteriosclerosis is the name of a group of diseases of the circulatory system that are characterized by hardening of the walls and the narrowing of the lumen (or opening) of an artery. In one form of arteriosclerosis, atherosclerosis, fatty streaks of plaque form on the inner walls of the artery. As the plaque accumulates and the streaks grow, the plaque deposits 2 begin to occlude the lumen 4 of the artery 6, as shown in FIG. 1. In time, the plaque deposits 2 may completely, or almost completely, occlude the lumen 4 of the artery 6, as shown in FIG. 2.

Arteries distribute oxygen-rich blood from the heart to cells of the body. The blood delivers oxygen to the cells and removes metabolic waste from the cells. Arteriosclerosis increases resistance to blood flow in the body because of the narrowed lumen and the hardened walls of the artery. The reduced blood flow causes cells served by the artery to be starved of oxygen and to experience an accumulation of toxic metabolic waste. The resistance to blood flow also causes blood pressure to increase, which may cause the heart to work harder to pump blood and, consequently, enlarge. Such a condition may lead to heart disease and heart failure.

Arteriosclerosis is treated by balloon angioplasty or coronary bypass surgery. In balloon angioplasty, a surgeon makes a small incision in a patient's groin area and inserts a balloon-tipped catheter into the patient's femoral artery. The balloon-tipped catheter is then advanced into the patient's heart and from there to the location of the occluded artery. The balloon is then repeatedly inflated and deflated, which causes the artery to expand and contract, until the surgeon determines that blood flow through the occluded artery has improved. The balloon-tipped catheter is then removed. In some cases, a cylindrical wire mesh, or "stent", is inserted in the artery after repeated inflation of the balloon to hold the artery open. Balloon angioplasty has become a routine surgical procedure. The recurrence rate of arteriosclerosis in patients that have undergone balloon angioplasty is high.

In coronary bypass surgery, veins from the patient's legs or other blood vessels are removed and used to replace the occluded portion of the artery. A surgeon opens the chest cavity by splitting the breastbone to access the heart and occluded artery. The vein that was removed from the patient is then attached at one end to the patient's aorta and at the other end to the blocked artery beyond the point of the occlusion. Consequently, the blood is allowed to bypass the occlusion in the artery.

When charged particles, such as electrolytes in blood (such as ions of sodium, calcium, potassium and magnesium), pass through a magnetic field they generate an electric current in the blood that heats the blood and causes blood vessels to expand. Further, the magnetic field causes the positive ions in the blood to deflect in one direction and the negative ions to deflect in the opposite direction. The resulting criss-crossing creates turbulence and eddy currents in the blood flow.

Magnets are also used to prevent the build-up of deposits on the inner surface of water pipes.

SUMMARY OF THE INVENTION

The invention provides a technique for preventing and treating arteriosclerosis that does not require interruption of blood flow through the affected artery and that has a continuing beneficial effect. Permanent magnets or electromagnets are implanted within the patient's body adjacent a fully or partially occluded artery or adjacent an artery in danger of developing an occlusion. The magnets are positioned such that at least a component of the magnetic flux generated by the magnets crosses the artery perpendicular to the direction of blood flow through the artery on the inflow side of the occlusion in the artery. The magnetic flux causes electrolytes in the blood to deflect from their original trajectories, which causes the normally laminar flow of blood to become turbulent at the site of the occlusion and beyond. The turbulence erodes the occlusion and reduces its size. Moreover, the turbulence inhibits the creation of occlusions. Further, the magnetic flux causes electric current to be conducted in the blood in the artery and in the plaque forming the occlusion. The resulting heat contributes to the reduction of the occlusion.

In general, in one aspect, the invention features an apparatus for treating and preventing arteriosclerosis in an artery in a human body. The artery has blood flowing through it in a blood flow direction. The apparatus comprises a first magnet, located inside the human body adjacent the artery. The first magnet generates magnetic flux through the artery. At least a portion of the magnetic flux has a component perpendicular to the blood flow direction.

Implementations of the invention may include one or more of the following. The magnetic flux having a component perpendicular to the blood flow direction may cover a cross-section of the artery. The portion of the magnetic flux having a component perpendicular to the blood flow direction may cover a portion, but not all, of the cross-section of the artery.

The apparatus may include a cuff, the cuff being configured to hold the first magnet adjacent an outside wall of the artery. The cuff may be separable to allow its implantation around the artery without severing the artery. The cuff may comprise a biocompatible material. The biocompatible material may comprise pyrolytic carbon. The pyrolytic carbon may comprise low temperature isotropic carbon. The pyrolytic carbon may comprise ultra low temperature isotropic carbon. The cuff may comprise a woven fabric and the first magnet may be woven into the fabric of the cuff.

The first magnet may be coated with a biocompatible material. The biocompatible material may comprise pyrolytic carbon. The pyrolytic carbon may comprise low temperature isotropic carbon. The pyrolytic carbon may comprise ultra low temperature isotropic carbon.

The apparatus may comprise one or more additional magnets located inside the human body adjacent the artery. The additional magnets may be configured to generate additional magnetic flux through the artery. At least some of the additional magnetic flux may have a component perpendicular to the blood flow direction. The first magnet and the additional magnets may be disposed in a ring around the circumference of the artery. The first magnet and the additional magnets may be distributed longitudinally along the artery. The first magnet and the additional magnets may be distributed around the circumference of the artery.

The apparatus may further comprise a separator for allowing the apparatus to be implanted around the artery without severing the artery. The separator may comprise a hinge. The first magnet may be embedded in a wrap. The wrap may comprise a biocompatible tube separable to allow it to be implanted around the artery without severing the artery. The apparatus may comprise additional magnets embedded in the wrap. The wrap may not constrict the artery during implantation. The apparatus may be implanted adjacent an inflow side of a partially occluded area of the artery.

The first magnet may be an electromagnet. The electromagnet may be powered by alternating current. The electromagnet may be powered by pulsed current. The pulsed current may be provided by a pacemaker. The pulsed current may be provided by a defibrillator.

The apparatus may further comprise a second magnet, located inside the human body adjacent the artery. The second magnet may cooperate with the first magnet to produce additional magnetic flux through the artery. At least a portion of the additional magnetic flux may have a component perpendicular to the blood flow direction. A mutual attraction between the first magnet and the second magnet may hold them adjacent to the artery.

In general, in another aspect, the invention features a method for treating and preventing arteriosclerosis in an artery in a human body, the artery having blood flowing through it in a blood flow direction. The method comprises implanting a magnet inside the human body adjacent the artery.

Implementations of the invention may include one or more of the following. Current flow in the blood may be induced by orienting the magnet so that a portion of its magnetic flux is perpendicular to the blood flow direction. Current flow through plaque formed on a wall of the artery may be induced.

In general, in another aspect, the invention features a method for treating and preventing arteriosclerosis in an artery in a human body, the artery having blood flowing through it in a blood flow direction. The method comprises implanting a magnet inside the human body adjacent the artery and creating turbulence in the blood by orienting the magnet to provide magnetic lines of flux having a component perpendicular to the blood flow direction.

Implementations of the invention may include one or more of the following. The method may comprise implanting one or more additional magnets inside the human body adjacent the artery. The method may comprise distributing the additional magnets longitudinally along the artery. The method may comprise distributing the additional magnets around the circumference of the artery. The method may comprise securing the magnets with a cuff. The method may comprise implanting the cuff without severing the artery.

BRIEF DESCRIPTION OF THE DRAWINGS

FIG. 5 is a cross-sectional view along lines V in FIG. 4.

FIG. 6 is a cross-sectional view along lines VI in FIG. 5.

FIG. 10 is a perspective view of an arteriosclerosis treatment and prevention apparatus according to the present invention.

FIG. 11 is a cross-sectional view along lines Xl of FIG. 10.

DESCRIPTION OF THE PREFERRED EMBODIMENTS

Figure 1:
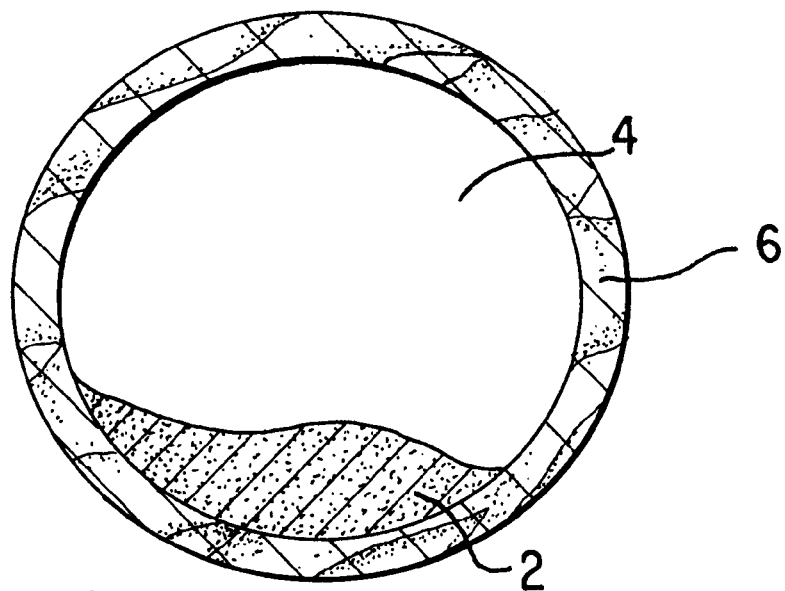
FIGS. 1 and 2 are cross-sectional views of partially occluded arteries.
Figure 2:
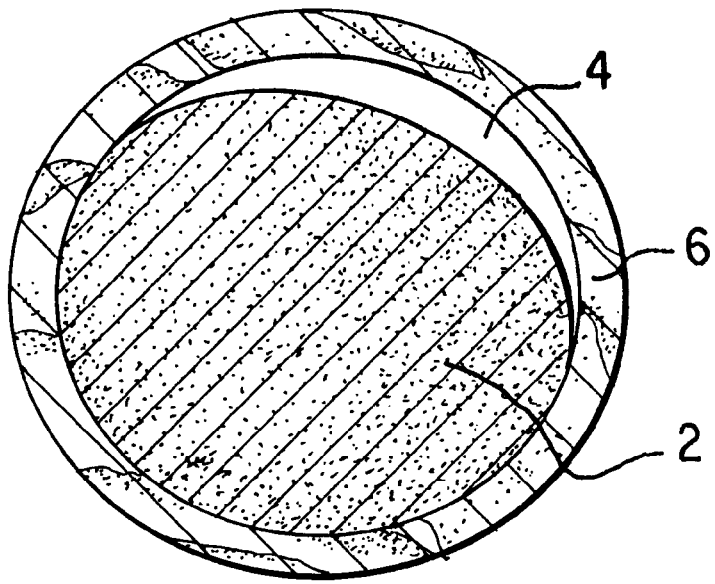
Figure 3:
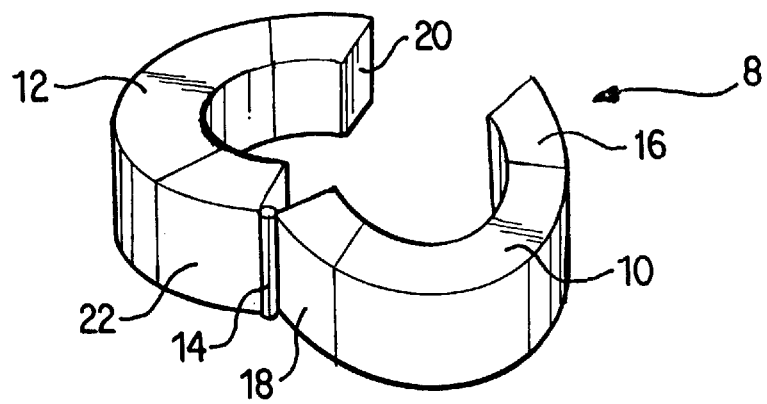
FIG. 3 is a perspective view of an arteriosclerosis treatment and prevention apparatus according to the present invention.

An arteriosclerosis prevention and treatment apparatus 8 comprises magnets 10 and 12 that are pivotally connected by a hinge 14, as illustrated in FIG. 3. The hinge 14 allows the magnets to pivot from an "open" position, as shown in FIG. 3, to a "closed" position, in which an orifice is formed between the magnets. Spacers 16, 18, 20 and 22, which are made from plastic or some other biocompatible non-ferrous material, prevent the magnets from contacting each other when the magnets are pivoted to the closed position. The spacers 16, 18, 20, and 22 can be reduced in size or even eliminated as long as some magnetic flux generated by magnets 10 and 12 crosses the orifice formed by magnets 10 and 12 in their closed position. The magnets 10 and 12 are positioned and selected so that when they are in the closed position the mutual attraction between the magnets 10 and 12 causes them to remain in the closed position.

The magnets are coated with a biocompatible substance such as pyrolytic carbon. The pyrolytic carbon can be either low temperature isotropic carbon such as PYROLITE® or ultra low temperature isotropic carbon such as BIOLITE®.

Figure 4:
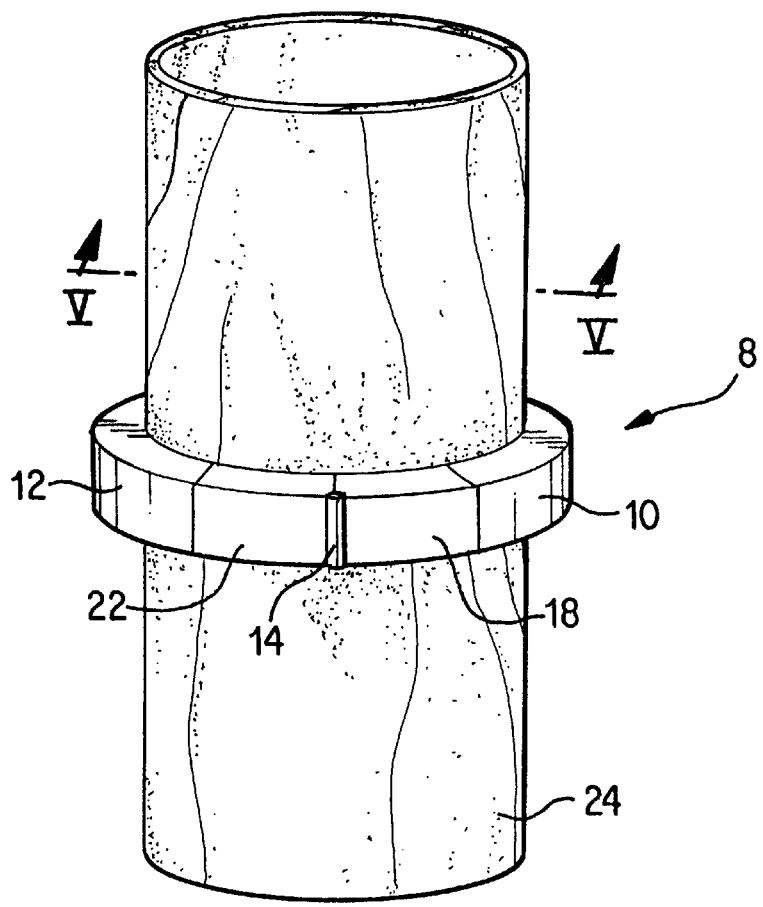
FIG. 4 is a perspective view of the invention of FIG. 3 implanted around an artery.

The apparatus 8 is positioned around the artery as shown in FIG. 4. This is accomplished by a surgeon opening the body of the patient to expose the artery 24 to be affected. The apparatus 8 is pivoted to its open position, placed around the artery 24, and pivoted to its closed position, illustrated in FIG. 4. It is not necessary to sever the artery 24 to implant the apparatus. Once the apparatus 8 is implanted as shown in FIG. 4, the mutual attraction between magnets 10 and 12 keeps it in place. It is not essential that the patient's body be opened to place the apparatus 8. Any technique that allows the apparatus to be placed as described above will suffice.

The apparatus 8 is placed on the inflow side of an occluding body 26, as shown in FIG. 5. Since the apparatus is on the inflow side of the occluding body, blood flowing through artery 24 will pass by apparatus 8 before it reaches occluding body 26.

There is a magnetic field between magnets 10 and 12. When the apparatus is in its closed position around the artery, as shown in FIG. 5, the magnetic flux 28 of the magnetic field crosses the orifice between the two magnets 10 and 12, as shown in FIG. 6. Since the artery is positioned within the orifice formed by the two magnets 10 and 12, the magnetic flux generated by the two magnets 10 and 12 crosses the lumen of the artery 24.

Blood carries electrolytes, which are ions of such elements as sodium, calcium, potassium and magnesium. Electrolytes are either positively charged or negatively charged. When the electrolytes pass through the magnetic flux 28 between magnets 10 and 12, the positively charged electrolytes 30 are deflected in one direction and the negatively charged electrolytes 32 are deflected in the opposite direction. The criss-crossing of the positively charged electrolytes 30 and the negatively charged electrolytes 32 creates turbulence and eddying 34 on the outflow side of the apparatus 8. The turbulence and eddying 34 act to erode the occluding object 26.

Further, the movement of the blood through the magnetic flux 28 causes an electric current to flow through the blood, warming it. The warming of the blood causes the artery 24 to expand, which reduces the resistance of the artery 24 to blood flow.

A portion of the magnetic flux 28 engages the occluding object 26, causing it to conduct electric current. The electric current through the object 26 warms it, which makes it more likely to erode under the influence of the turbulence and eddying 34.

The amount the positive and negative electrolytes 30 and 32 deflect from trajectories prior to encountering the magnetic flux 28 is dependent on the strength of the magnetic flux 28 through the artery 24 and the orientation of the magnetic flux 28 relative to the direction of the blood flow.

The strength of magnetic flux diminishes in inverse proportion to the square of the distance from the magnet. Thus, by placing the magnets 10 and 12 adjacent the artery 24, the magnetic flux 28 inside the artery 24 is greater than if the magnets 10 and 12 were outside the body.

Figure 7:
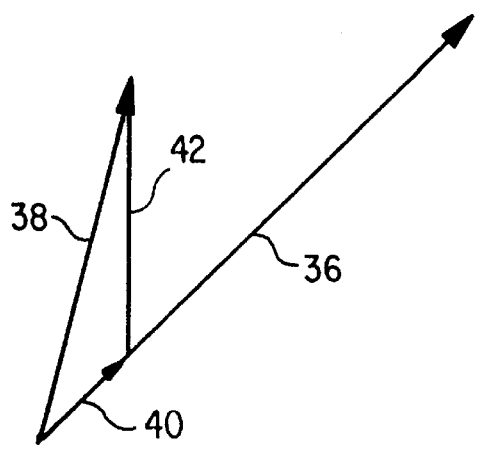
FIG. 7 is a vector diagram.

The effect of the magnetic flux 28 is greatest where the direction of blood flow is perpendicular to the direction of blood flow. Placing the magnets 10 and 12 on opposite sides of artery 24 causes the magnetic flux through the lumen of the artery 24 to be generally perpendicular to the direction of blood flow, as shown in FIG. 6. Even where the magnetic flux 24 is not perpendicular to the direction of blood flow, the magnetic flux 28 will have some effect because the magnetic flux 28 will generally have a component perpendicular to the direction of blood flow, as shown in FIG. 7. Vector 36 represents the direction and magnitude of blood flow at a specific point within the lumen of artery 24. Vector 38 represents the direction and magnitude of the magnetic flux 28 through that same point. Vector 36 is not perpendicular to vector 38 but can be resolved into two vectors 40 and 42, which are parallel and perpendicular to the direction of blood flow, respectively. The portion of the magnetic flux represented by vector 42, which is perpendicular to the direction of blood flow, will create turbulence and will cause electric current to flow through the blood. The portion of the magnetic flux represented by vector 40 will have neither effect. Therefore, as long as magnets 10 and 12 are situated so that some component of the magnetic flux is perpendicular to the direction of blood flow, the desired turbulence will be achieved.

Moreover, it is not essential that the magnetic flux cover the entire lumen of the artery 24. Beneficial results will be achieved even if only a portion of the lumen is exposed to the magnetic flux.

Figure 8:
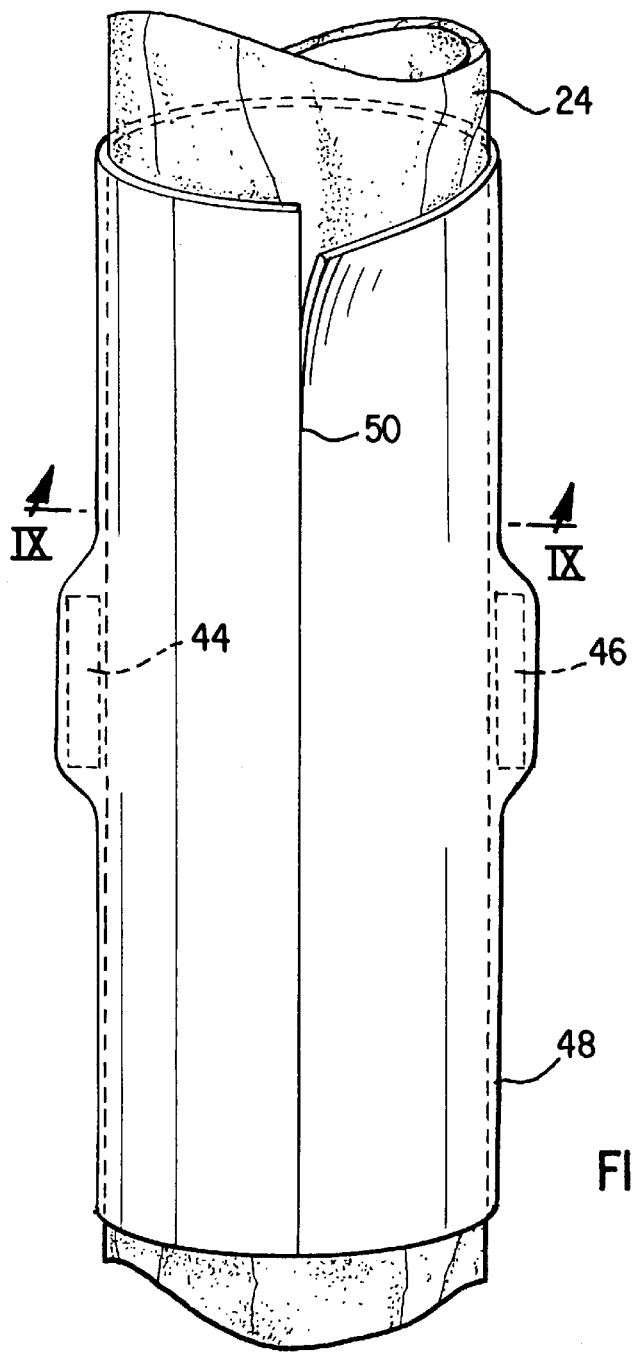
FIG. 8 is a perspective view of an arteriosclerosis treatment and prevention apparatus according to the present invention.

The magnets 44 and 46 may also be held in place adjacent the artery by a wrap 48, as illustrated in FIG. 8. The wrap 48 is a flexible material coated with a biocompatible material such as PYROLITE® or BIOLITE®. The wrap 48 has a seam 50 that allows it to be separated and placed around artery 24 without severing the artery 24. The wrap 48 is sufficiently rigid that it does not constrict the artery 24 as it is being secured around the artery. After the magnets 44 and 46 are secured in place by the wrap 48, the seam 50 is closed by sutures or some other securing device.

Figure 9:
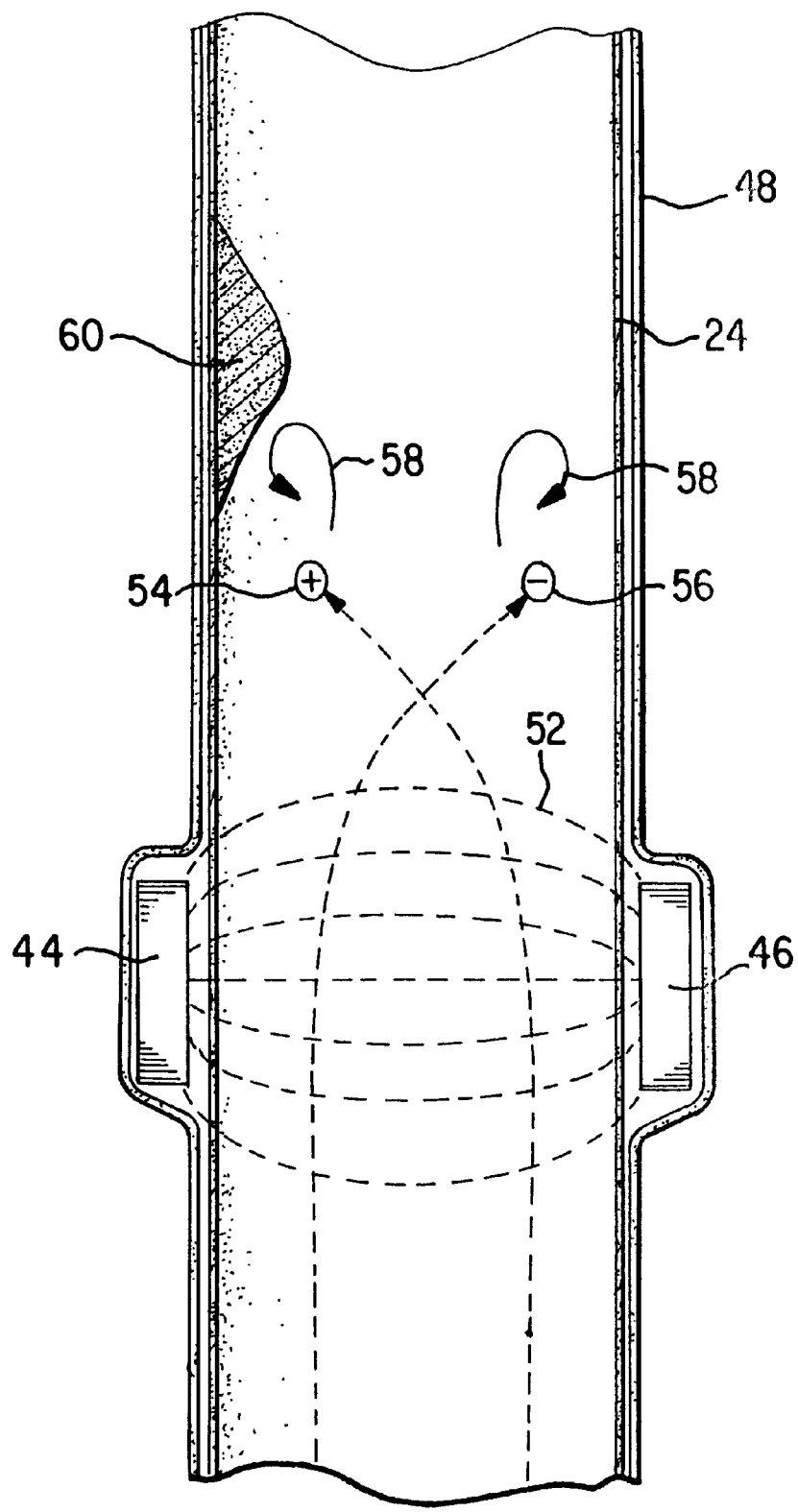
FIG. 9 is a cross-sectional view along lines IX in FIG. 8.

The arrangement shown in FIG. 8 produces a similar effect to the arrangement of FIG. 4, as illustrated in FIG. 9. Magnets 44 and 46 are held adjacent the artery 24 by wrap 48, producing magnetic flux 52 between the magnets 44 and 46. Positively charged electrolytes 54 that pass through the magnetic flux 52 are deflected in one direction and negatively charged electrolytes 56 that pass through the magnetic flux 52 are deflected in the opposite direction. The resulting criss-crossing produces turbulence and eddying 58 which erodes the occluding body 60. Further, electric current is generated in the blood and in the occluding body 60, producing the beneficial results described above.

More than two magnets can be used to create the magnetic flux, as illustrated in FIG. 10. Wrap 48 holds magnets 62 in a ring adjacent artery 24. The resulting magnetic flux 64 in the lumen of the artery 24 is the magnetic flux of each individual magnet 62, as shown in FIG. 11, plus any interaction between the magnets 62 (not shown). The passage of blood through the magnetic flux produces the turbulence and beneficial effects described above.

Figure 12:
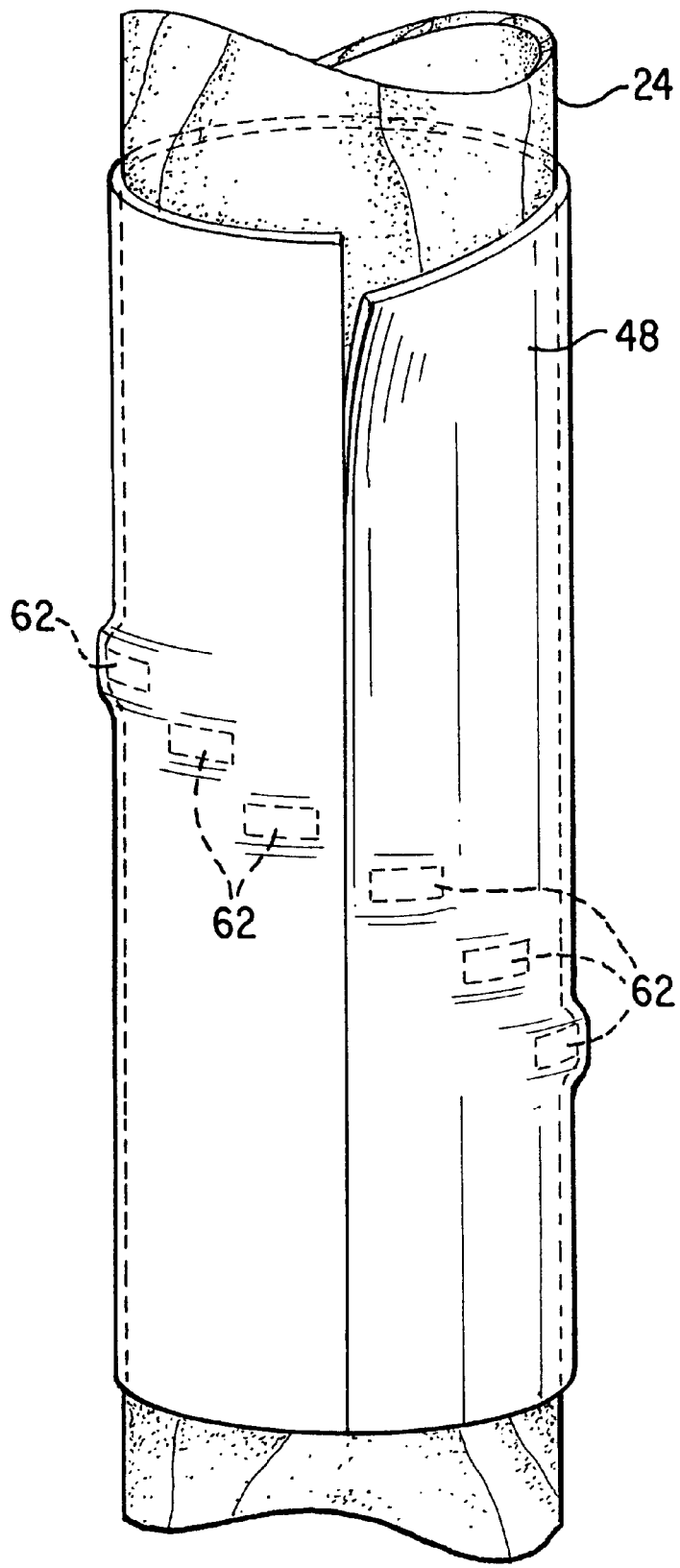
FIG. 12 is a perspective view of an arteriosclerosis treatment and prevention apparatus according to the present invention.

The magnets 62 can also be distributed longitudinally along the artery 24, as shown in FIG. 12. This has the effect of distributing the magnetic flux longitudinally along the artery 24. The same turbulence and beneficial effect will be produced.

Figure 13:
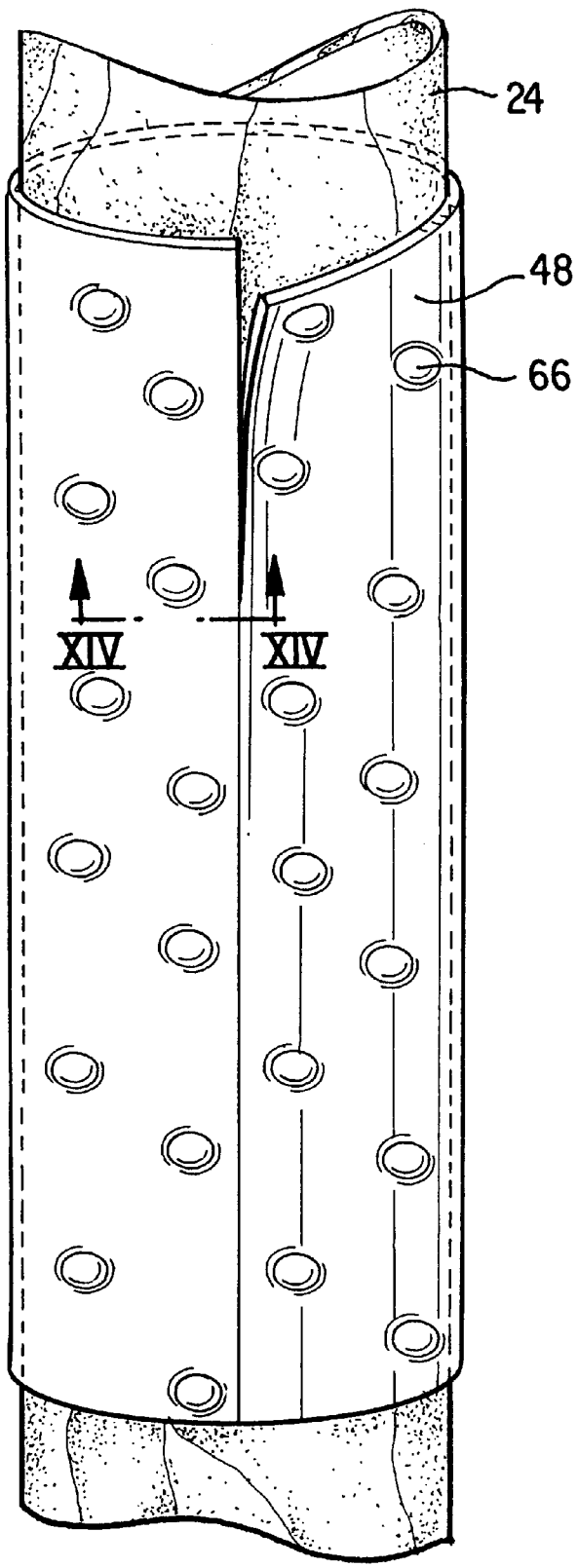
FIG. 13 is a perspective view of an arteriosclerosis treatment and prevention apparatus according to the present invention.

The magnets 66 can be distributed in any pattern that produces magnetic flux perpendicular to the direction of blood flow within the lumen of the artery 24, as illustrated in FIG. 13.

Figure 14:
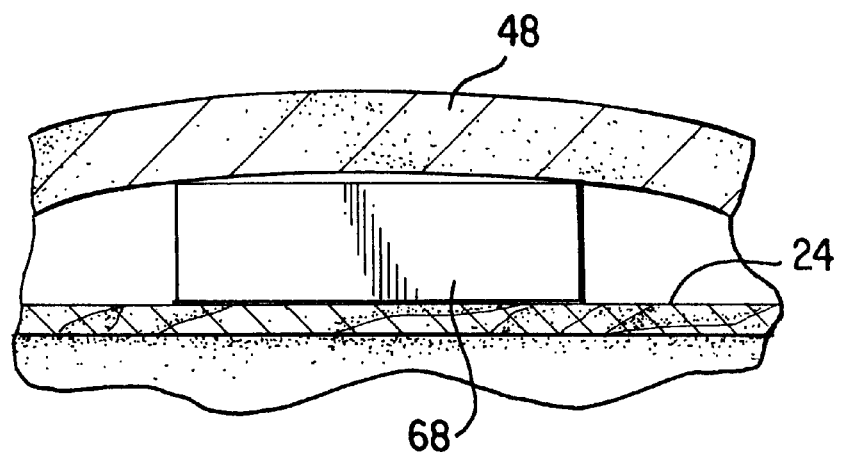
FIG. 14 is a cross-sectional view along lines XIV of FIG. 13.
Figure 15:
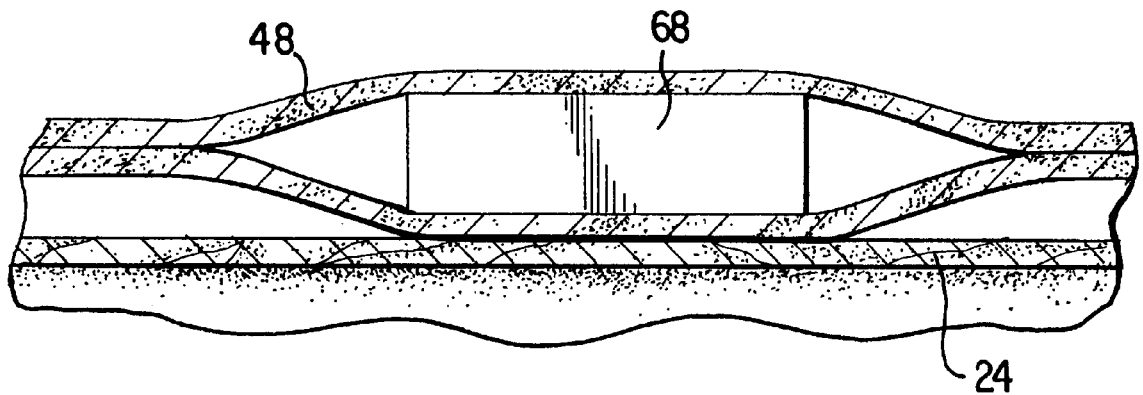
FIG. 15 is a cross-sectional view along lines XIV of FIG. 13.

The magnets 68 can be separate from the wrap 48, as illustrated in FIG. 14, or they can be woven into or otherwise embedded in the wrap 48, as illustrated in FIG. 15.

Figure 16:
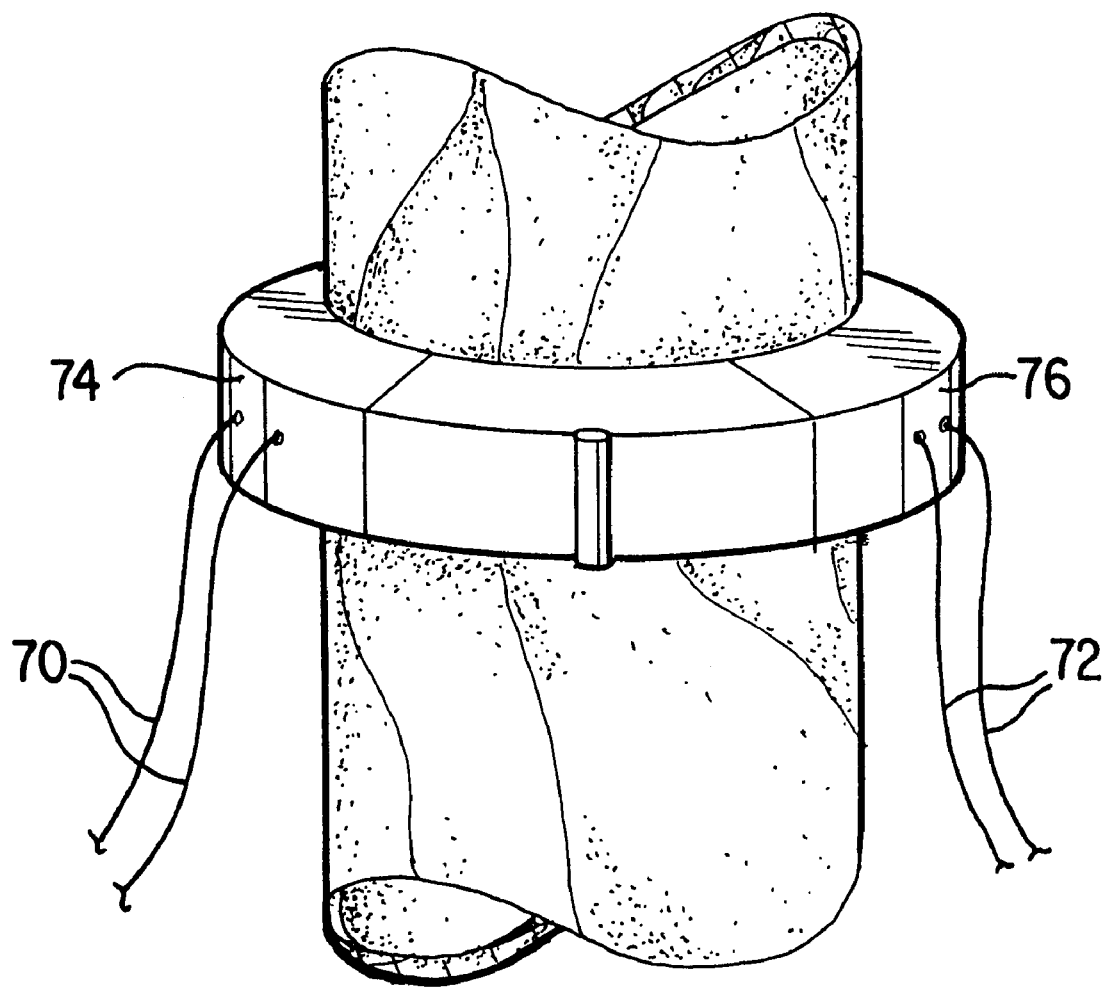
FIG. 16 is a perspective view of an arteriosclerosis treatment and prevention apparatus according to the present invention.
Figure 17:
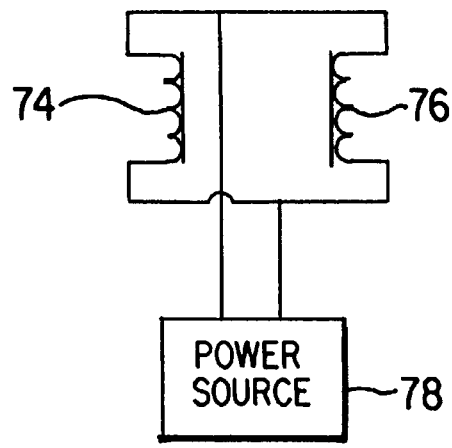
FIGS. 17, 18, 19, and 20 are schematic diagrams.

The magnets can be either permanent magnet, as shown in FIG. 4, or electromagnets, as shown in FIG. 16. Leads 70 and 72 provide power to the electromagnets 74 and 76, respectively. A power source 78 provides power to the electromagnets 74 and 76, as illustrated in FIG. 17. The power source 78 can provide direct current, alternating current or pulsed current.

Figure 18:
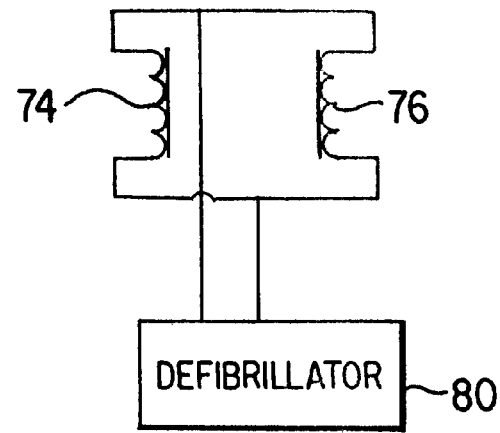
Figure 19:
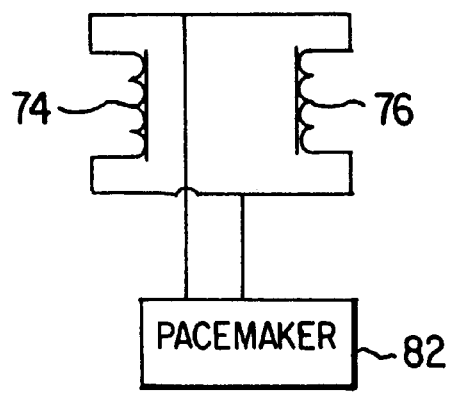
Figure 20:
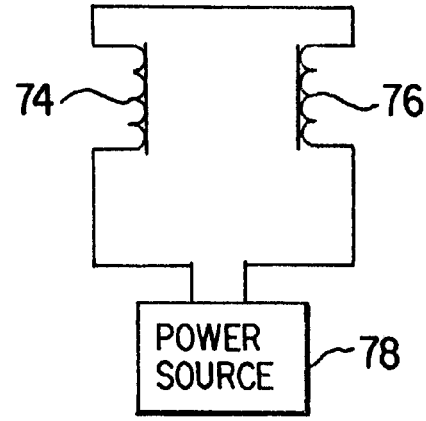

Examples of power sources capable of producing pulsed power are a defibrillator 80, as shown in FIG. 18, or a pacemaker 82, as shown in FIG. 19, or any other source of power. The electromagnet coils can be wired in parallel, as shown in FIG. 17, or in series, as shown in FIG. 20.

The magnets illustrated in FIGS. 8, 10, 12, and 13 may all be either permanent magnets or electromagnets or they can be a mixture of permanent magnets and electromagnets.

The foregoing describes preferred embodiments of the invention and is given by way of example only. The invention is not limited to any of the specific features described herein, but includes all variations thereof within the scope of the appended claims.

What is claimed is:

1. An apparatus for treating and preventing arteriosclerosis in an artery in a human body, the artery having blood flowing through it in a blood flow direction, the apparatus comprising a first magnet, located inside the human body adjacent the artery, the first magnet generating magnetic flux through the artery; and at least a portion of the magnetic flux having a component perpendicular to the blood flow direction.

2. The apparatus of claim 1 wherein the artery has a cross-section; and the portion of the magnetic flux having a component perpendicular to the blood flow direction covers the cross-section of the artery.

3. The apparatus of claim 1 wherein the artery has a cross-section; and the portion of the magnetic flux having a component perpendicular to the blood flow direction covers a portion, but not all, of the cross-section of the artery.

4. The apparatus of claim 1 further comprising a cuff, the cuff being configured to hold the first magnet adjacent an outside wall of the artery.

5. The apparatus of claim 4 wherein the cuff is separable to allow its implantation around the artery without severing the artery.

6. The apparatus of claim 4 wherein the cuff comprises a biocompatible material.

7. The apparatus of claim 6 wherein the biocompatible material comprises pyrolytic carbon.

8. The apparatus of claim 7 wherein the pyrolytic carbon comprises low temperature isotropic carbon.

9. The apparatus of claim 7 wherein the pyrolytic carbon comprises ultra low temperature isotropic carbon.

10. The apparatus of claim 4, wherein the cuff comprises a woven fabric; and the first magnet is woven into the fabric of the cuff.

11. The apparatus of claim 1, wherein the first magnet is coated with a biocompatible material.

12. The apparatus of claim 11 wherein the biocompatible material comprises pyrolytic carbon.

13. The apparatus of claim 12 wherein the pyrolytic carbon comprises low temperature isotropic carbon.

14. The apparatus of claim 12 wherein the pyrolytic carbon comprises ultra low temperature isotropic carbon.

15. The apparatus of claim 1 further comprising one or more additional magnets located inside the human body adjacent the artery;

the additional magnets configured to generate additional magnetic flux through the artery;

at least some of the additional magnetic flux having a component perpendicular to the blood flow direction.

16. The apparatus of claim 15 wherein the first magnet and the additional magnets being disposed in a ring around the circumference of the artery.

17. The apparatus of claim 15 wherein the first magnet and the additional magnets being distributed longitudinally along the artery.

18. The apparatus of claim 17 wherein the first magnet and the additional magnets being distributed around the circumference of the artery.

19. The apparatus of claim 1 further comprising a separator for allowing the apparatus to be implanted around the artery without severing the artery.

20. The apparatus of claim 19 wherein the separator comprises a hinge.

21. The apparatus of claim 1 wherein the first magnet is embedded in a wrap, the wrap comprising a biocompatible tube separable to allow it to be implanted around the artery without severing the artery.

22. The apparatus of claim 21 further comprising additional magnets embedded in the wrap.

23. The apparatus of claim 21 wherein the wrap does not constrict the artery during implantation.

24. The apparatus of claim 1 wherein the apparatus is implanted adjacent an inflow side of a partially occluded area of the artery.

25. The apparatus of claim 1 wherein the first magnet is an electromagnet.

26. The apparatus of claim 25 wherein the electromagnet is powered by alternating current.

27. The apparatus of claim 25 wherein the electromagnet is powered by pulsed current.

28. The apparatus of claim 27 wherein the pulsed current is provided by a pacemaker.

29. The apparatus of claim 27 wherein the pulsed current is provided by a defibrillator.

30. The apparatus of claim 1 further comprising a second magnet, located inside the human body adjacent the artery, the second magnet cooperating with the first magnet to produce additional magnetic flux through the artery; and at least a portion of the additional magnetic flux having a component perpendicular to the blood flow direction.

31. The apparatus of claim 30 wherein a mutual attraction between the first magnet and the second magnet hold them adjacent to the artery.

32. A method for treating and preventing arteriosclerosis in an artery in a human body, the artery having blood flowing through it in a blood flow direction, the method comprising implanting a magnet inside the human body adjacent the artery.

33. The method of claim 32 further comprising inducing current flow in the blood by orienting the magnet so that a portion of its magnetic flux is perpendicular to the blood flow direction.

34. The method of claim 32 further comprising inducing current flow through plaque formed on a wall of the artery.

35. A method for treating and preventing arteriosclerosis in an artery in a human body, the artery having blood flowing through it in a blood flow direction, the method comprising implanting a magnet inside the human body adjacent the artery; and creating turbulence in the blood by orienting the magnet to provide magnetic lines of flux having a component perpendicular to the blood flow direction.

36. The method of claim 35 further comprising implanting one or more additional magnets inside the human body adjacent the artery.

37. The method of claim 36 further comprising distributing the additional magnets longitudinally along the artery.

38. The method of claim 37 further comprising distributing the additional magnets around the circumference of the artery.

39. The method of claim 35 further comprising securing the magnets with a cuff.

40. The method of claim 39 further comprising implanting the cuff without severing the artery.

\* \* \* \* \*